US011793739B2

(12) United States Patent
Colver et al.

(10) Patent No.: US 11,793,739 B2
(45) Date of Patent: Oct. 24, 2023

(54) HAIR SHAPING MATERIAL

(71) Applicant: Croda International Plc, Goole (GB)

(72) Inventors: Patrick James Colver, Goole (GB); Neil Howard James, Goole (GB); Christopher Michael Carr, Leeds (GB); David Malcolm Lewis, Leeds (GB); Peter Jeffrey Broadbent, Leeds (GB); Muriel Laure Aude Rigout, Leeds (GB)

(73) Assignee: Croda International Plc, Goole (GB)

( * ) Notice: Subject to any disclaimer, the term of this patent is extended or adjusted under 35 U.S.C. 154(b) by 0 days.

(21) Appl. No.: 16/495,856

(22) PCT Filed: Mar. 27, 2018

(86) PCT No.: PCT/EP2018/057735
§ 371 (c)(1),
(2) Date: Sep. 20, 2019

(87) PCT Pub. No.: WO2018/178056
PCT Pub. Date: Oct. 4, 2018

(65) Prior Publication Data
US 2020/0069548 A1  Mar. 5, 2020

(30) Foreign Application Priority Data

Mar. 28, 2017 (GB) ..................... 1704905
Nov. 10, 2017 (GB) ..................... 1718602

(51) Int. Cl.
*A61K 8/44* (2006.01)
*A61K 8/46* (2006.01)
*A61K 8/64* (2006.01)
*A61Q 5/00* (2006.01)
*A61Q 5/04* (2006.01)

(52) U.S. Cl.
CPC .............. *A61K 8/447* (2013.01); *A61K 8/466* (2013.01); *A61K 8/64* (2013.01); *A61Q 5/002* (2013.01); *A61Q 5/04* (2013.01); *A61K 2800/40* (2013.01)

(58) Field of Classification Search
None
See application file for complete search history.

(56) References Cited

U.S. PATENT DOCUMENTS

| 4,948,876 | A | | 8/1990 | Bore et al. |
| 5,424,062 | A | * | 6/1995 | Schwan ................ A61K 8/463 424/70.2 |
| 5,679,819 | A | * | 10/1997 | Jones ................ D06M 15/6436 424/78.17 |
| 2014/0044664 | A1 | * | 2/2014 | Cardamone .............. A61P 5/02 424/70.14 |
| 2017/0143611 | A1 | * | 5/2017 | Hippe .................. A61K 8/8176 |
| 2019/0201307 | A1 | | 7/2019 | Knuebel et al. |

FOREIGN PATENT DOCUMENTS

| CN | 103664709 A | 3/2014 |
| JP | 05125037 A | 5/1993 |
| JP | 2006265201 A | 10/2006 |
| JP | 2006342063 A | 12/2006 |
| WO | 2018041439 A1 | 3/2018 |

OTHER PUBLICATIONS

International Search Report and Written Opinion for International Application No. PCT/EP2018/057735 dated Jul. 6, 2018, 11 pages.
Japanese Notice of Reasons for Refusal for Japanese Application No. 2019-553032, dated Sep. 28, 2021, with translation, 7 pages.

* cited by examiner

*Primary Examiner* — Danah Al-Awadi
(74) *Attorney, Agent, or Firm* — RatnerPrestia

(57) ABSTRACT

The present invention relates to novel hair treatment materials, and in particular materials for shaping hair and/or strengthening the hair. Also described are the use of these compounds in hair care formulations for shaping, straightening, strengthening or treating the hair, and the use of the compounds for hair straightening and/or hair strengthening.

9 Claims, No Drawings

HAIR SHAPING MATERIAL

CROSS REFERENCE TO RELATED APPLICATIONS

This application is the National Stage filing of International Appln. No. PCT/EP2018/057735, filed Mar. 27, 2018, and claims priority of GB Application No. 1704905.7, filed Mach 28, 2017 and GB Application No.: 1718602.4, filed Nov. 10, 2017, the entirety of which applications is incorporated herein by reference for all purposes.

The present invention relates to novel hair treatment materials, and in particular materials for shaping hair and/or strengthening the hair.

Current systems for treating and shaping hair are often based on formaldehyde and glyoxylic acid combinations. Both materials are harmful and not pleasant to use by the consumer.

The mechanical strength or protein structure of keratin fibres, either from animal or human source, can be measured using a number of different techniques. These techniques can give information on different elements of the keratin fibres which can all ultimately relate to the strength of the fibres. Fundamentally, the force required to break a fibre, or a number of fibres, would be classed as its strength. This force is a result of the chemical bonds present in the protein material. As with most organic materials, and especially proteins with their varied side chains resulting from different amino acid make up, there are a number of different types of bonding that can be present, e.g. covalent bonds such as peptide bonds, disulphide bonds etc, ionic bonds formed between acidic and basic amino acid side chains and hydrogen bonds. Each of these types of bonds will exert a different force due to their relative bond energy and abundance, but in total they make up the entirety of the measured "strength".

It is common practice both in the textile and personal care field to treat fibrous materials in ways in which their physical properties can be altered to suit a desired end need. For example, in personal care, hair fibres or more precisely the melanin pigment within the fibre, can be oxidised using a hydrogen peroxide containing system in order to modify the colour of the fibre. Alternatively, high temperatures in excess of 180° C. or chemicals such as sodium hydroxide or similar high pH treatments can be used to modify the curl patters of hair fibres by changing the internal bonding and structure of the protein. In the case of high temperatures, primarily hydrogen bonding is disrupted and this results in a temporary change to the hair as this type of bond is easily broken and reformed. However some of the stronger bonds in the hair are also broken over multiple heat cycles and these do not reform over time, resulting in more severe damage accumulating in the hair. High pH treatments are even more severe as the mechanism here is to break the strong disulphide bond in the hair while a mechanical shape re-arrangement is performed. A neutralising treatment results in the reformation of most of the covalent bonds (a mono-sulphide not a disulphide) but not all of the bonds will be reformed.

All of these treatments are applied across the whole hair fibre and are therefore non-specific to a certain bond type or structural component within the hair. As such, side reactions take place which are not intentional and can result in further unintentional bond breakage and as a result hair is damaged and loss of strength occurs.

There is a continual requirement for improved hair care actives and end-use products containing such actives. One such product category are those which improve hair straightening. Another product category are those that improve hair strength, and those which claim to repair the hair after damaging treatments.

There is a need for a hair straightening effect to be obtained from the use in hair care products, and to develop a straightening material which is safer and less harmful to use. There is also a need for a product which has hair strengthening properties which is safer and less harmful to use.

The present invention seeks to provide hair straightening and/or strengthening compounds, the use of these compounds in hair care formulation, and use of the compounds for hair straightening and/or hair strengthening.

According to a first aspect of the present invention there is provided a Bunte salt of cystine, wherein the molecular weight (weight average) of the Bunte salt is in the range from 100 to 1,600 Daltons.

According to a second aspect of the present invention there is provided a Bunte salt of cystine, wherein the percentage of cystine Bunte salt present in the bulk of material is in the range from 1 wt. % to 6 wt. %.

According to a third aspect of the present invention there is provided a method of preparing a Bunte salt of cystine according to the first aspect, said method comprising hydrolysing a protein to provide a molecular weight (weight average) of 100 to 1,600 Daltons, and forming a Bunte salt with the hydrolysed protein.

According to a fourth aspect of the present invention there is provided a hair care, hair straightening, hair strengthening and/or hair treatment formulation comprising a Bunte salt of cystine, where the molecular weight (weight average) of the Bunte salt is in the range from 100 to 1,600 Daltons.

According to a fifth aspect of the present invention there is provided the use of a Bunte salt of cystine for use in straightening of hair, where the molecular weight (weight average) of the Bunte salt is in the range from 100 to 1,600 Daltons.

According to a sixth aspect of the present invention there is provided the use of a Bunte salt of cystine to strengthen hair, where the molecular weight (weight average) of the Bunte salt is in the range from 100 to 1,600 Daltons.

According to a seventh aspect of the present invention there is provided a method of treating hair, the method which includes the steps of
 combining a Bunte salt of cystine comprising formulation with an acid having pH of 2-6;
 applying said combination to hair;
 applying a heated element to the treated hair;
 washing treated hair; and
 optionally repeating any of the above steps.

It has been found that use of Bunte salts of cystine when used in hair care formulations provide desired hair straightening properties and hair strengthening properties, and overcomes the above mentioned problems.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, the term 'Bunte salt' is well known in the field and refers to compounds having functional group $RSSO_3^-$ and derived from the oxidative sulphitolysis of cystine.

The Bunte salt of cystine may be formed from individual amino acids, or from amino acids comprised within longer peptide chains that are derived from hydrolysed protein.

Preferably the cystine may be part of an amino acid chain formed from hydrolysed protein.

The individual amino acids which may be used to form Bunte salts comprise at least one cystine. The amino acid blend may include other non-cystine amino acids and these may be selected from any suitable amino acid.

The amino acid is preferably a single amino acid. In an alternative embodiment the amino acid may comprise a chain of two or more amino acids. The amino acid chain length is preferably from 2 to 5.

In an alternative embodiment the cystine used for forming the Bunte salt may be derived from protein which has been hydrolysed to form shorter peptide chains and amino acids.

The protein component starting material which is used to form the Bunte salt of the present invention may be derived from either animal or vegetable sources, or by fermentation. Examples of proteins which may be used include collagen, elastin, keratin, casein, wheat protein, potato protein, soya protein, and/or silk protein. Keratin protein is particularly preferred.

The term "protein" is used herein to include both native (or chemically unmodified) and hydrolysed proteins, and thus comprises proteins properly so-called and polypeptides, peptides, amino acids and/or peptones, since the latter may all be categorised as hydrolysed proteins. Hydrolysed proteins are preferred, particularly polypeptides and peptides, which may for example be produced by acid, alkali, and/or enzyme hydrolysis, of native proteins. Acid hydrolysed proteins are preferred. In one embodiment, hydrolysed keratin proteins are preferred, in particular produced by acid hydrolysis.

Chemically modified proteins and/or hydrolysed proteins may also be employed, for example where the protein has been covalently reacted with a functional group, e.g. a silane, a quaternary ammonium compound and/or an acid chloride.

In an alternative embodiment protein from milled wool may be used where the protein is not pre-treated and not pre-hydrolysed or solubilised prior to acid hydrolysis.

It will be understood that the protein component is a mixture of amino acids and short protein chains, small peptides.

The molecular weight (weight average) of the protein component starting material (prior to hydrolysis) may vary over a wide range, such as for example in the range from 100 to 500,000 Daltons. Molecular weight average will be understood to be a measurement of the value across the whole range of amino acid comprising compounds in the Bunte salt, and would include both reacted and unreacted proteins. Once hydrolysed, the protein or polypeptide comprises on average in the range from 2 to 10, preferably 2 to 8, more preferably 2 to 5 amino acids.

The composition of the amino acids in the protein component can also be an important parameter, and in one embodiment the protein comprises at least 0.5%, preferably in the range from 1 to 15%, more preferably 2 to 8%, particularly 2 to 6%, and especially 3 to 5% w/w of cysteine or cystine based amino acids. This would include any cys species present such as —S—$SO_3$ (Bunte salt), cystine, cysteine, cysteic acid and the like.

It will be understood that the amino acid profile of a protein may be readily determined by hydrolysing the protein completely to amino acids then analysing.

The amino acid profile of the protein would be understood to remain the same or substantially the same from protein starting material, to hydrolysed protein, to Bunte salt comprising material.

Preferably where the amount of free amino acid in the hydrolysed protein is less than 60 wt. %. More preferably less than 55 wt. %. It will be understood that as the free amino acid has low solubility it is desired that the amount is at a low level.

The molecular weight (weight average) of the total material including Bunte salt is suitably in the range from 100 to 1,600, preferably 120 to 1,200, more preferably 140 to 1,000, particularly 170 to 800, and especially 200 to 500 Daltons.

The molecular weight (weight average) is preferably substantially unchanged between the hydrolysed state and the total material including Bunte salt. Preferably, the molecular weight (weight average) is within 15%, more preferably 10%, most preferably 5%.

The molecular weight (weight average) is measured using size-exclusion HPLC (SE-HPLC), the conditions of which are detailed below:

Column—TSK-GEL G2000SWx1 (300 mm×7.8 mm internal diameter)
Guard column—TSK SWx1 (40 mm×6 mm internal diameter)
Pump—Agilent 1260 quaternary pump VL (G1311C)
Injector—HP1100 series autosampler (G1313A)
Thermostat—HP1100 series thermostatted column compartment (G1316A)
Detector—HP1100 series variable wavelength detector (G1314A)
Control—Agilent Chemstation software
Integration—Agilent Cirrus GPC software
Eluent—0.05M $KH_2PO_4$, 0.06M $K_2HPO_4·3H_2O$ and 0.1M NaCl adjusted to pH 7.0
Flow rate—0.6 ml/minute
Injection volume—5
Temperature—25° C.
Wavelength—220 nm
Standards—Bovine albumin (67 kDa), egg albumin (45 kDa), chymotrypsin (25 kDa), and glycine (75 Da)
Calibration fit type—Cubic splines The amount of cys based protein/amino acid which will react to form Bunte salts is about 50% therefore the amount of Bunte salt present is about 2 wt. %.

The Bunte salt may be formed by firstly hydrolysing the desired protein. The hydrolysis may preferably be acid hydrolysis.

The hydrolysis performed will be to the extent required to achieve the desired molecular weight and chain length of the hydrolysed protein. The degree of hydrolysis may be varied by varying the temperature, amount and/or strength of acid used, and time taken.

The hydrolysed protein may be filtered and treated to remove undesired material. In particular the hydrolysed protein may be treated to remove any chloride ions present.

The hydrolysed protein may be reacted with a sulphite comprising compound to form Bunte salt. In particular alkali metal metabisulphite may be use, and most preferably sodium metabisulphite is used to form the Bunte salt.

The pH of the Bunte salt may be adjusted to the desired range. One advantage of the Bunte salt material is that it can be used at higher pH values compared to many prior materials. The Bunte salt may be used at a pH value in the range from 3.0 to 6.0, and preferably 4.0 to 5.0.

The amino acid profile of the hydrolysed protein mixture preferably stays substantially the same after Bunte salt reaction.

It will be understood that in the protein used there is cystine which is naturally occurring and is formed from two cysteine molecules joined together. Cysteine does not react with a bisulphite to form a Bunte salt whereas cystine does. Cystine reacts to form one Bunte salt molecule and one cysteine molecule so theoretically only 50% converts to Bunte salt. However, cysteine may crosslink back with other cysteine molecules to form cystine which can then react further with bisulphite.

The Bunte salt comprising material may be added in to a formulation for use in hair care, hair straightening, hair strengthening and/or hair treatment.

The formulation may be in the form of a hair care product such as a shampoo, conditioner, 2-in-1 shampoo/conditioner, hairspray, hair spritz, hair colouring product, leave-on hair tonic, hair sunscreen product, styling mousse or gel, hair styling cream, styling treatments, or other hair treatment composition.

Alternatively the formulation may in the form of a hair treatment be made in situ, and this may be achieved by providing the Bunte salt material in a two pot form, with a first pot comprising Bunte salt material, urea, sodium sulphite, and other components as listed below, and a second pot comprising acid, preferably citric acid. The first pot is preferably at a pH of about 7. The acidic second pot would be added to the first pot just prior to use and lowers the pH to about 4-5 thereby enabling reaction of the first pot content with the keratin/hair when applied.

The formulation according to the present invention may suitably comprise in the range from 0.01 wt. % to 20 wt. %, preferably 0.5 wt. % to 10 wt. %, more preferably 1 wt. % to 8 wt. %, and especially 2 wt. % to 6 wt. % of the Bunte salts, based on the total weight of the composition. Most preferably, 5.0 wt. %.

The formulation may comprise one or more surfactants. The surfactants may be selected from anionic, non-ionic, amphoteric and/or cationic surfactants. Preferably, the surfactants may be a non-ionic and/or anionic surfactants.

Suitable anionic surfactants include alkyl sulphates, alkyl ether sulphates, alpha olefin sulphonates, sulphosuccinates, isethionates, acyl amides, acyl glutamates, alkyl ether carboxylates and alkyl phosphates. The alkyl group preferably comprises in the range from 6 to 30, more preferably 8 to 20, particularly 10 to 14, and especially 12 carbon atoms. Alkyl ether sulphates and/or alkyl sulphates are preferred, particularly alkali metal, e.g. sodium, and/or ammonium salts thereof. Phosphate based anionic surfactants are particularly preferred anionic surfactants.

Suitable non-ionic surfactants include the fatty alcohol acid or amide ethoxylates, alkanolamides and alkoxylated alkanolamides, monoglyceride ethoxylates, sorbitan ester ethoxylates, alkyl polyglycosides, ethylene glycol monoesters, ethylene glycol diesters, and mixtures thereof.

Suitable amphoteric surfactants include alkylimino-dipropionates, alkylamphoglycinates, alkylamphopropionates, alkylamphoacetates (mono- and di-), N-alkyl beta-aminopropionic acids, alkylpolyamino carboxylates, phosphorylated imidazolines, and mixtures thereof.

Suitable cationic surfactants include alkyl quaternaries, benzyl quaternaries, ester quaternaries, ethoxylated quaternaries, alkyl amines, and mixtures thereof. The alkyl group preferably comprises in the range from 6 to 30, more preferably 8 to 22, and particularly 10 to 20 carbon atoms.

If present, the surfactants may be included in an amount ranging from 0.1 wt. % to 50 wt. % by weight, preferably from 5 wt. % to 30 wt. %, more preferably from 10 wt. % to 25 wt. % by weight of the total formulation.

The formulation can also include other acceptable ingredients, such as those which are suitable for topical application to the hair.

The formulation can be mixed with or diluted by an excipient. The excipient may serve as a diluent, it can be a solid, semi-solid, or liquid material, which acts as a vehicle, carrier or medium for the active ingredient. Examples of suitable excipients include: lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

The formulation may additionally comprise: lubricating agents such as talc, magnesium stearate, and mineral oil; wetting agents; emulsifying and suspending agents; preserving agents such as methyl- and propylhydroxy-benzoates; sweetening agents; and flavouring agents.

The formulation may be formulated as transparent or opaque emulsions, lotions, creams, pastes or gels.

The formulation may comprise water. The amount of the water in the formulation may suitably be in the range from 10 wt. % to 97 wt. %, preferably 30 wt. % to 95 wt. %, more preferably 50 wt. % to 90 wt. %, particularly 65 wt. % to 85 wt. %, and especially 72 wt. % to 78 wt. %, based on the total weight of the formulation.

The formulation of the present invention may be used with one or more of the other standard ingredients or carriers used in hair care products, including shine enhancers, moisturisers, herbal additives, hair strengtheners, vitamin additives, colorants, hair thickening agents; setting and styling agents; ultraviolet absorbers; silicone oils; essential oils and fragrances; thickening or viscosity-enhancing agents; detergents; stabilising agents; emollients; chelating agents; sequestering agents; preservatives; disinfectants; anti-oxidants/radical scavengers; antistatic agents; conditioning agents; detangling ingredients; emulsifying or dispersing agents; stimulants; soothers; solvents; carriers and the like.

In particular, the formulation may comprise a silicone fluid or oil such as dimethylpolysiloxane, dimethyl silicone, highly polymerised methyl polysiloxane, and methyl polysiloxane, known generically as dimethicone, cyclic oligomeric dialkylsiloxanes, such as the cyclic oligomers of dimethylsiloxane, known generically as cyclomethicone. The concentration of silicone oil in the formulation may preferably be in the range from 0.1 wt. % to 40 wt. %, more preferably 0.3 wt. % to 20 wt. %, particularly 0.5 wt. % to 5 wt. %, and especially 1 wt. % to 1.5 wt. % based on the total weight of the formulation.

The formulation may be in the form of an aqueous "leave on" or an aqueous "rinse off" end-use product. For such formulations, a dilute solution may be used. Preferably, a buffered solution is used, in which the pH of the solution is adjusted to mildly acidic, with a pH in the range of from 4 to 6. In the case of rinse-off formulations, instructions are provided to wash off the diluted formulation after application. Depending on the level of treatment required, such instructions may also require the product to remain on the hair for some time, such as from 1 to 30 minutes. For leave-on formulations, the washing off step is omitted.

Where the formulation is a hair shampoo or conditioner which functions to make the hair straighter, the shampoo or conditioner may be in the form of a dispersion, emulsion or solution. One preferred system is one that forms liquid crystals. The liquid crystals are preferably lyotropic liquid crystals (i.e. both concentration and temperature dependent), more preferably lamellar phase liquid crystals, and particularly L alpha phase (neat) liquid crystals.

The formulation may contain many different types of functional ingredients such as;
  (i) cationic hair conditioning agents, e.g. ethoxylated phosphate fatty quats, such as those sold by Croda as Arlasilk™; fatty amido amines, such as those sold by Croda as Incromine™; fatty quats, such as those sold by Croda as Incroquat™ Crodazosoft™, Rejuvasoft™ or VibraRiche™ typically used at a concentration in the range from 1 wt. % to 5 wt. % based on the total weight of the composition. These are typically combined with polymeric hair conditioning cationic materials such as quaternised cellulose sold by Croda as Crodacel™, quaternised proteins, such as those sold by Croda, as Croquat™, Crolactin™, Crosilkquat™, Keramimic™ and Hydrotriticum™.
  (ii) fatty alcohols, e.g. stearyl, cetearyl, cetyl, oleyl alcohols, used typically at a concentration range of 2 wt. % to 5 wt. % based on the total weight of the composition.
  (iii) humectants or solvents, e.g. alcohols and polyols such as glycerol and polyethylene glycols, when used typically at a concentration in the range from 1 wt. % to 10 wt. % based on the total weight of the composition;
  (iv) reconstructors, e.g. hydrolysed proteins such as wheat protein, which function to penetrate the hair and strengthen the hair structure through polymer cross-linking;
  (v) glossing or detangling materials which bind to the hair and reflect light, e.g. silicones such as dimethicone, phenyltrimethicone, dimethiconol and/or trimethylsilylamodimethicone, usually at a concentration in the range from 0.2 wt. % to 10 wt. % based on the total weight of the composition;
  (vi) acidity regulators, e.g. citric acid, lactic acid, which generally maintain the pH of the conditioner at about 4 to 6;
  (vii) thermal protectors, usually heat-absorbing polymers, which shield the hair against excessive heat, e.g. caused by blow-drying or curling irons or hot rollers such as for instance those sold by Croda as Mirustyle™ MFP (quaternised starch); and
  (viii) UV protection agents, to protect hair or formulation components from degradation by UV light, such as those sold by Croda as Crodasorb™ UV-HPP.

In one embodiment, the formulation of the invention is in the form of an emulsion (or dispersion), such as an oil-in-water or water-in-oil emulsion, particularly an oil-in-water emulsion.

The oil phase of the emulsion will preferably be mainly an emollient oil of the type used in personal care or cosmetic products. The emollient can and usually will be an oily material which is preferably liquid at ambient temperature. Alternatively, it can be solid at ambient temperature, in which case in bulk it will usually be a waxy solid, provided it is liquid at an elevated temperature at which it can be included in and emulsified in the composition.

Suitable normally liquid emollient oils include non-polar oils, for example mineral or paraffin, especially isoparaffin, oils, such as that sold by Croda as Arlamol™ HD; or medium polarity oils, for example vegetable ester oils such as jojoba oil, vegetable glyceride oils, animal glyceride oils, such as that sold by Croda as Crodamol™ GTCC (caprylic/capric triglyceride), synthetic oils, for example synthetic ester oils, such as isopropyl palmitate and those sold by Croda as Estol™ 1512, ether oils, particularly of two fatty e.g. C8 to C18 alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as Arlamol™ E (propoxylated stearyl alcohol).

The concentration of the oil phase may vary widely. The amount of the oil phase in the emulsion is preferably in the range from 0.5 wt. % to 80 wt. %, more preferably 1 wt. % to 30 wt. %, particularly 1.5 wt. % to 15 wt. %, and especially 2 wt. % to 10 wt. %, based on the total weight of the emulsion.

The amount of the aqueous phase in the emulsion is preferably in the range from 20 wt. % to 99.5 wt. %, more preferably 70 wt. % to 99 wt. %, particularly 85 wt. % to 98.5 wt. %, and especially 90 wt. % to 98 wt. %, based on the total weight of the emulsion.

A wide range of emulsifiers may be employed, particularly one or more non-ionic emulsifier(s). The specific nature of the emulsifier surfactant used in any particular instance depends on the type of emulsion being made, particularly the amount and nature of the oil being emulsified and the total desired level of emulsifier.

The concentration of emulsifier in the emulsion is preferably in the range from 0.1 wt. % to 20 wt. %, more preferably 0.5 wt. % to 15 wt. %, particularly 1 wt. % to 10 wt. %, and especially 2 wt. % to 7 wt. %, based on the total weight of the emulsion.

The emulsion suitably comprises in the range from 0.01 wt. % to 10 wt. %, preferably 0.5 wt. % to 5 wt. %, more preferably 0.1 wt. % to 4 wt. %, particularly 0.2 wt. % to 2 wt. %, and especially 0.3 wt. % to 1 wt. % of the hair care formulation based on the total weight of the emulsion.

Many other components that may be used in the formulations according to the present invention. These components may be oil soluble, water soluble or non-soluble. Examples of such materials include:
  (i) preservatives such as those based on parabens (alkyl esters of 4-hydroxybenzoic acid), phenoxyethanol, substituted ureas and hydantoin derivatives, e.g. those sold commercially under the trade names Germaben II, Nipaguard BPX and Nipaguard DMDMH, when used usually in a concentration in the range from 0.5 wt. % to 2 wt. % based on the total weight of the composition;
  (ii) perfumes, when used typically at a concentration in the range from 0.1 wt. % to 10 wt. % more usually up to about 5 wt. % and particularly up to about 2 wt. %, based on the total weight of the composition;
  (iii) humectants or solvents such as alcohols, polyols such as glycerol and polyethylene glycols, when used typically at a concentration in the range from 1 wt. % to 10 wt. % based on the total weight of the composition;
  (iv) alpha hydroxy acids such as glycolic, citric, lactic, malic, tartaric acids and their esters; self-tanning agents such as dihydroxyacetone;
  (v) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F, e.g. as polyunsaturated fatty acid esters such as gamma-linolenic acid esters;
  (vi) skin care agents such as ceramides either as natural materials or functional mimics of natural ceramides;
  (vii) natural phospholipids, e.g. lecithin;
  (viii) vesicle-containing formulations;

(ix) botanical extracts with beneficial skin care properties;
(x) skin whiteners such as kojic acid, arbutin and similar materials;
(xi) skin repair compounds actives such as Allantoin and similar series;
(xii) caffeine and similar compounds;
(xiii) cooling additives such as menthol or camphor;
(xiv) insect repellents such as N,N-diethyl-3-methylbenzamide (DEET) and citrus or eucalyptus oils;
(xv) essential oils; and
(xvi) pigments, including microfine pigments, particularly oxides and silicates, e.g. iron oxide, particularly coated iron oxides, and/or titanium dioxide, and ceramic materials such as boron nitride, or other solid components, such as are used in make-up and cosmetics, to give suspoemulsions, typically used in an amount in the range from 1 wt. % to 15 wt. %, but usually at least 5 wt. %, and particularly about 10 wt. % based on the total weight of the formulation.

The formulations may comprise a fragrance-imparting material to provide a pleasant scent. In one aspect, a scent is provided from a natural source, such as but not limited to alfalfa, almond, amber, angelica root, anise, apple, apricot, banana, basil, bay, bay laurel, benzoin, bergamot, bitter orange, black pepper, bois de rose (rosewood), cajeput, cardamom, carrot seed, cedarwood, cinnamon, citronella, citrus, clary sage, clove, cocoa, coconut, coffee, coriander, cranberry, cypress, elemi, eucalyptus globulous, eucalyptus, fennel, frankincense, galbanum, geranium, German chamomile, ginger, grapefruit, helichrysum, hyssop, jasmine, juniper berry, lavender, lemon, lemongrass, lily, linden blossom, mango, marjoram, melissa, mint, myrrh, myrtle, neroli, niaouli, nutmeg, orange, oregano, palm, parsley, patchouli, peach, peppermint, petitgrain, pine, pineapple, raspberry, Roman chamomile, rose, rosemary, sandalwood, spearmint, spruce, strawberry, tea, thyme, vanilla, vetiver, violet, yarrow, ylang ylang, and the like. Preferably, the fragrance is selected from mint or vanilla.

One preferred method of treating hair comprises the steps of;
combining a Bunte salt comprising formulation with an acid having pH of 2-6;
applying said combination to hair;
applying a heated element to the treated hair;
washing treated hair; and
optionally repeating any of the above steps.

These steps may be repeated, in order to obtain the desired hair straightening effect.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

EXAMPLES

Example 1—Bunte Salt Synthesis

Water (793 g) and hydrochloric acid (28%, 342 g) were mixed in a glass reactor vessel and heated to 60° C. Milled wool fibres (600 g) were slowly added to the hot acid while stirring until all the fibres were wetted by the acid. After adding the wool, the reaction mixture was heated to 120° C. to hydrolyse the wool.

The contents of the vessel were then heated to reflux for 7 hours. After this time the reaction mixture was cooled to room temperature and filtered. The filter cake was washed with water until the wash water showed a refractive index of 0%. The washings and filtrate were collected and passed through an anion exchange column to remove the chloride ions.

The low ash solution was then mixed with activated carbon (90 g) and stirred for 4 hours. The carbon was then filtered out and the solution was carbon treated for a second time. The protein solution was then evaporated to a refractive index of approximately 35% and preserved.

Sodium metabisulphite was added to the protein solution and the pH adjusted to 5.0-5.5 before mixing vigorously for 24 hours. Hydrogen peroxide (35%) was then added to the product prior to final pH adjustment and filtration.

Example 2—Test Formulation

A series of test formulations were made according to the following generic formulation:

TABLE 1

| Test formulation A | |
| --- | --- |
| Ingredient | % w/w |
| Water (deionised) | To 100 |
| Urea | 2 |
| Sodium Sulfite | 5 |
| Bunte Active of Example 1 | 5 (% active) |
| Citric acid (50%) | To pH 4.5 |

The Bunte active used had a Mw of 173 Da using the SE-HPLC method as defined herein.

TABLE 2

| Test Formulation B | |
| --- | --- |
| Ingredient/INCI Name | % w/w |
| Part A | |
| Brij S2 (Steareth-2)[1] | 5.00 |
| Brij S721 (Steareth-21)[1] | 2.00 |
| Crodacol CS50 (Cetearyl Alcohol)[1] | 1.75 |
| Mineral Oil 25cS at 25° C. | 1.50 |
| Part B | |
| Pricerine 9091 (Glycerin)[1] | 3.00 |
| Keltrol CG-SFT (Xanthan Gum)[4] | 1.50 |
| Part C | |
| Water Deionised (Aqua) | To 100 |
| Sodium Sulphite | 2.50 |
| Urea | 2.00 |
| Part D | |
| Bunte salt of Cystine (Example 1) | 26.88 |
| Peppermint Cool Fragrance[2] | 2.00 |
| Euxyl PE9010 (Phenoxyethanol (and) Ethylhexylglycerin)[3] | 0.80 |

Test Formulation B was prepared by pre-mixing the Part B ingredients and combining the Part C ingredients with stirring until dissolved. Part B was then added to Part C with stirring. The Part A ingredients were then mixed and heated to 65-70° C. The Part BC mixture was also heated to the same temperature as Part A and then added to Part A with stirring. The heat was removed and once the mixture had reached 40° C., Part D was added with stirring. The resulting formulation was stirred to cool.

The following comparative formulation was also made to act as a benchmark with test formulations A and B.

Comparative formulation 1 (C1) (negative benchmark)—water (pH 4.5)

Example 3—Hair Straightening Test Protocol

The formulations were subjected to the following test protocol to evaluate the effectiveness as a hair straightening agent.

Materials

Curly Hair Swatches (Brazilian, IHIP. L250 mm, W5 mm)

Round Brush

Flat Irons (GHD model 4.2 B)

Hair Dryer

Hair Treatment

Hair used was selected to have a prominent curl. The hair to be used was washed once with basic shampoo (0.5 mL) rinsed (30 s) and allowed to dry naturally. A photo of the hair swatch was taken as a "Before Treatment" record.

The hair swatch was then laid flat in 100 mL of the test solution and covered in cling film. The hair was left in the solution for 30 minutes, and then the swatch was combed through once every 10 minutes for a total of 30 minutes. Any excess solution was removed from the swatch via squeezing (twice) and then blotted on a paper towel. The hair was dried with a hair dryer and round barrel brush until approximately 80-90% dry which took around 30 seconds.

The treated hair swatch was straightened with flat irons for five passes, each under maximum tension. Each pass took seven seconds and a wide tooth comb was used to direct the hair when ironing.

Maintenance Step

The swatch was washed with basic shampoo (0.5 mL) and rinsed (30 seconds). The hair was dried with a hair dryer and round barrel brush until approximately 80-90% dry which took around 30 seconds. The treated hair swatch was straightened with flat irons for five passes, each under maximum tension. Each pass took seven seconds and a wide tooth comb was used to direct the hair when ironing. The hair switch was photographed as a record for "After Treatment".

Straightness Retention Step

The swatch was washed with basic shampoo and rinsed. The swatch was combed through once and then allowed to dry naturally. The swatch was then photographed, with this labelled as '1 Wash'.

The Straightness Retention process was repeated a further 29 times to give a total of 30 washes. Photographs were taken at 1, 5, 10, 15, 20, 25 and 30 washes.

Results

After being treated the hair swatch was measured both in terms of length and width. The shorter and wider the hair swatch the curlier the hair, and therefore this indicated limited hair straightening. A hair swatch which was longer and narrower was therefore an indication of hair that had been treated with an effective hair straightener. Hair straightness may also be assessed visually.

TABLE 3

Hair straightening results

| Swatch | Length (cm) | | Width (cm) | |
|---|---|---|---|---|
| | A | C1 | A | C1 |
| Before | 20.13 | 19.2 | 4.28 | 9.87 |
| After | 22.58 | 23.75 | 3.16 | 3.59 |
| 1 Wash | 22.09 | 21.07 | 3.3 | 7.4 |
| 5 Wash | 26.01 | 20.68 | 3.99 | 10.69 |
| 10 Wash | 22.94 | | 3.99 | |
| 20 Wash | 22.49 | | 5.48 | |
| 30 Wash | 24.05 | | 4.7 | |

As can be seen from the results, the treated hair has greater length and less width that the hair washed with the comparative. This clearly indicates the hair remains straighter and curls less when treated with the material of the present invention. The effect can also be seen to last for several washes after the treatment meaning time between repeat treatments may be longer than seen with prior art materials.

Example 4—Hair Strengthening Test Protocol

A—Tensile Strength

Tensile testing is possibly the most common way of evaluating hair strength as it involves physically pulling hair fibres and measuring the resisting force up until the fibre breaks. Although the break point can be measured, other tensional parameters can be measured as the hair is placed under tensile stress.

Materials and Equipment

Automatic crimper (AAS1600 by Dia-Stron or similar sample preparation equipment)

Laser micrometer (Dia-Stron LSM-5000 or equivalent)

Tensile tester (Dia-Stron MTT690 or equivalent)

Humidity controlled chamber/room, set at 50% relative humidity (RH) (for assessment of dry hair properties)

Brass tabs

Hair tresses (Brazilian hair with curl type III) that have been prepared by being bleached 3 times.

Treatment

Test Formulation B detailed in the table above, and Comparative Formulation C1, were applied to separate samples of 3-times bleached Brazilian hair with curl type III, saturating the hair tresses by applying the equivalent of 2.5 g of formulation per gram of hair. The saturated hair tresses were then left to rest for 30 minutes at ambient temperature and humidity, to ensure disruption to the maximum number of disulphide bonds within the hair and allow optimum time for actives to penetrate the hair fibre. Following this rest period, and before removing the formulation, the hair tresses were blow dried until completely dry. The hair tresses were then straightened using 10 passes of thermal straightening irons over the length of the tresses (Babyliss, 210° C.). The hair tresses were then left to rest for 15 minutes before being washed with a simple shampoo, blow dried until completely dry and then straightened using 10 passes of the thermal straightening irons once again. Finally, the hair tresses were left to rest for 5 days before being evaluated.

Procedure

Dry Hair Measurements 1. 30 to 50 hair fibres per treatment were prepared by crimping the fibres individually between brass tabs using the automatic crimper.

2. The fibres were equilibrated at 50% RH for 2 hr.
3. The fibre diameter was measured using the laser micrometer. This was done by taking 3 measurements along the length of the hair fibre to obtain an average value representative of the entire fibre.
4. The fibres were equilibrated again at 50% RH for 2 hr.
5. The strain rate in the tensile tester was set to 20 mm/min.
6. Each fibre was then strained up to the fracture point using the tensile tester and the measurements from the tensile tester recorded. Average (mean) results were calculated using results from each fibre.

Wet Hair Measurements
1. 30 to 50 hair fibres per treatment were prepared by crimping the fibres individually between brass tabs using the automatic crimper.
2. The prepared fibres were soaked in DI water for at least 30 min.
3. The fibre diameter was measured using the laser micrometer. This was done by taking 3 measurements along the length of the hair fibre to obtain an average value representative of the entire fibre.
4. The fibres were individually placed in the tensile tester's cassette and the pockets filled with DI water to soak the fibres, making sure there was no overflow.
5. The strain rate in the tensile tester was set to 20 mm/min.
6. Each fibre was then strained up to the fracture point using the tensile tester and the measurements from the tensile tester recorded. Average (mean) results were calculated using results from each fibre.

Results

In the tensile strength measurements, a higher result is reflective of a higher tensile strength. From the results in Table 4 below, it can be seen that the treatment of bleached hair fibres with Test Formulation A leads to an improved/increased tensile strength over the untreated, bleached hair.

TABLE 4

Tensile strength results

| Wet/Dry Hair Fibres | Measurement | Comparative Formulation C1 | Test Formulation B |
|---|---|---|---|
| Dry | Average Young's Modulus | 4.08E+09 Pa | 4.20E+09 Pa |
| Wet | Average Young's Modulus | 1.10E+09 Pa | 1.22E+09 Pa |
| Wet | Average Plateau Stress | 3.74E−03 gmf/sq. micron | 4.19E−03 gmf/sq. micron |
| Wet | Average Break Stress | 1.51E−02 gmf/sq. micron | 1.68E−02 gmf/sq. micron |
| Wet | Average Postyield Gradient | 4.47 gmf/mm | 4.96 gmf/mm |

B—Differential Scanning Calorimetry

Differential Scanning calorimetry uses the measurement of heat flow to determine structural changes as a result of increasing temperature. Although not a direct evaluation of hair strength, a higher temperature at which the proteins within a hair fibre denature indicates more a more intact protein structure. Damaging treatments, such as those mentioned above, lead to a reduction in the denaturation temperature which correlates well with tensile testing measurements as well as consumer feedback relating to poorer quality, weaker hair with more breakage.

Materials & Equipment
Differential Scanning calorimeter (DSC)
Hair tresses (Brazilian hair with curl type III)
High pressure, high volume aluminium pans
Products/formulations to be tested Operating Parameters:
Temperature range: 50° C. to 190° C. (no dehydration/water evaporation step needed) Heating rate: 10° C./min Treatment
Hair tresses were prepared for the DSC measurements in the same way as described above for the tensile strength test. In addition to the 3-times bleached samples treated with Test formulation B and Comparative Formulation C1, this test involved the use of virgin hair sample, ie those which had not been bleached or subjected to any other treatment steps.

Sample Preparation
1. For each treatment to be evaluated, about 100 mg of hair was cut into ~2 mm sections (hair resembled a powder at this particle size).
2. The hair "powders" were stored at constant relative humidity (45%) overnight.
3. 5-7 mg of hair powder was weighed into large volume-pressure resistant stainless steel capsules. Three capsules were prepared for each treatment to be evaluated in order for an average (mean) to be calculated.
4. 50 microliters of deionized water was added to each capsule using a micropipette.
5. The capsules were sealed and stored overnight for equilibration.
6. The denaturation enthalpy was then measured for each capsule sample using the DSC.

Results

For the DSC results, a higher denaturation temperature (Td) value represents more structure within the hair. The results are shown below in Table 5. The hair structure is damaged by bleach, so a higher value result, indicating increased structure, is a sign of the strengthening of the hair structure.

TABLE 5

DSC results

| Td (° C.) | Capsule 1 | Capsule 2 | Capsule 3 | average Td (° C.) |
|---|---|---|---|---|
| Virgin hair | 154.91 | 155.17 | 155.34 | 155.14 |
| Comparative Formulation C1 | 149.26 | 148.72 | 148.65 | 148.88 |
| Test Formulation B | 157.7 | 157.54 | 157.71 | 157.65 |

Example 5—Formulation Examples

Strong and Straight Shampoo

| Ingredients | % |
|---|---|
| Part A | |
| Deionized Water | To 100 |
| Dissodium EDTA | 0.10 |
| Part B | |
| Sodium Laureth Sulfate (27% active solution) | 15.00 |
| Crodasinic LS 30 (Aqua (and) Sodium Lauroyl Sarcosinate) | 10.00 |
| Crodateric CAB 30 (Aqua (and) Cocamidopropyl Betaine) | 8.00 |

-continued

| Ingredients | % |
|---|---|
| Arlasilk PLN (Linoleamidopropyl PG-Dimonium Chloride Phosphate Dimethicone (and) Aqua) | 1.00 |
| Dimethiconol (and) TEA-Dodecylbenzenesulfonate | 2.00 |
| Part C | |
| Crodapearl ™ AF (Water & Sodium Laureth Sulphate & Glycol Distearate) | 3.50 |
| Crothix ™ liquid (PEG-150 Pentaerythrityl Tetrastearate (and) Aqua (and) PEG-6 Caprylic/Capric Glycerides) | 4.20 |
| Bunte salt of Cystine (Example 1) | 3.00 |
| Preservative | 0.50 |
| Fragrance | 0.50 |
| Part D | |
| Citric Acid | To pH 5.50-6.50 |

Suppliers: 1: Croda

Procedure

The ingredients of parts A and B were mixed separately, with moderate stirring. Part A was added to part B with moderate stirring. The ingredients of phase C were then added, in the order described. The pH was adjusted, if necessary, using part D.

Hair Strengthening Cream Conditioner

| Ingredients | % |
|---|---|
| Part A | |
| Water Deionized | To 100 |
| Disodium EDTA | 0.05 |
| Glycerine | 1.00 |
| Part B | |
| Incroquat Behenyl TMS 50 (Cetearyl Alcohol and Behentrimonium Methosulfate)[1] | 2.00 |
| Crodazosoft DBQ (Quaternium-91 (and) Cetrimonium Methosulfate (and) Cetearyl Alcohol)[1] | 1.30 |
| Cetearyl Alcohol | 3.00 |
| Crodamol STS (PPG 3 Benzyl Ether Myristate)[1] | 1.00 |
| KeraDyn HD ((Bis-Ethyl(isostearylimidazoline) Isostearamide)[1] | 0.50 |
| Dimethicone | 0.50 |
| Part C | |
| Bunte salt of Cystine (Example 1) | 5.00 |
| Phenoxyethanol | 0.50 |
| Fragrance | 0.50 |

Suppliers: 1. Croda

Procedure

Part A and Part B were combined separately and heated to 75-80° C. The oil phase was then slowly added to the water phase with stirring and once added, the stirring was maintained for about 10 minutes. The mixture was then stirred slowly to cool down. Once cool, Part C was added, and the pH adjusted, if necessary.

It is to be understood that the invention is not to be limited to the details of the above embodiments, which are described by way of example only. Many variations are possible.

The invention claimed is:

1. A hair treatment formulation comprising a hydrolysed protein which comprises a Bunte salt of cystine,
    wherein the cystine is present in an amino acid chain of the hydrolysed protein, the hydrolysed protein having an average molecular weight range of 100 to 500 Daltons,
    wherein the hydrolysed protein which comprises a Bunte salt of cystine is present in the hair treatment formulation in about 5 wt. %,
    wherein the hair treatment formulation comprises about 2 wt. % urea based on the total weight of the formulation and 2.5 wt. % to 5 wt. % sodium sulphite based on the total weight of the formulation, and
    wherein curled hair treated with the hair treatment formulation is straighter than curled hair treated with a corresponding hair treatment formulation not containing the Bunte salt.

2. A method of treating hair, comprising applying the hair treatment formulation according to claim 1 to hair.

3. A method of straightening hair, comprising applying the hair treatment formulation according to claim 1 to hair.

4. The hair treatment formulation according to claim 1, wherein the formulation also strengthens hair.

5. The hair treatment formulation according to claim 1, wherein the formulation further comprises non-ionic and/or anionic surfactants.

6. The hair treatment formulation according to claim 5, wherein the non-ionic and/or anionic surfactants are present in an amount of 5 wt. % to 30 wt. % by weight of the total formulation.

7. The hair treatment formulation according to claim 1, wherein the formulation further comprises a silicone fluid or oil.

8. The hair treatment formulation according to claim 7, wherein the silicone fluid or oil is present in an amount of 0.3 wt. % to 20 wt. % by weight of the total formulation.

9. The hair treatment formulation according to claim 1 in combination with an acid having a pH of 2 to 6.

* * * * *